United States Patent [19]

Jonas et al.

[11] 4,070,357
[45] Jan. 24, 1978

[54] PROCESS FOR THE PREPARATION OF INDOLINE DERIVATIVES

[75] Inventors: Rochus Jonas; Rudolf Klug, both of Darmstadt, Germany

[73] Assignee: Merck Patent Gesellschaft mit beschraenkter Haftung, Darmstadt, Germany

[21] Appl. No.: 653,846

[22] Filed: Jan. 30, 1976

[30] Foreign Application Priority Data

Feb. 4, 1975 Germany .................. 2504531

[51] Int. Cl.² .................................. C07D 487/04
[52] U.S. Cl. .................. 260/268 TR; 260/289 H; 260/326.11 R; 424/250
[58] Field of Search .................. 260/268 TR

[56] References Cited

U.S. PATENT DOCUMENTS

| | | | |
|---|---|---|---|
| 3,317,524 | 5/1967 | Freed | 260/246 |
| 3,853,878 | 12/1974 | Jonas et al. | 260/268 TR |

*Primary Examiner*—Alton D. Rollins
*Assistant Examiner*—Jose Tovar
*Attorney, Agent, or Firm*—Millen & White

[57] ABSTRACT

Novel indoline derivatives of the formula

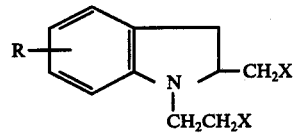

I wherein R is H or CH₃O and the X each are Cl or Br or collectively are —N(CH₂C₆H₅)— or acid addition salts thereof are obtained by treating a 3-hydroxy-1,2,3,4-tetrahydroquinoline of the formula

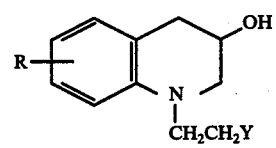

II with an inorganic acid halide and, if appropriate, the reacting resulting dihalogen compound with benzylamine or converting a resulting acid addition salt by treatment with a base in the free base or converting a free base by treatment with an acid to an acid addition salt.

5 Claims, No Drawings

PROCESS FOR THE PREPARATION OF INDOLINE DERIVATIVES

BACKGROUND OF THE INVENTION

The invention relates to a new process for the preparation of indoline derivatives, which are intermediates for the preparation of 1,2,3,4,10,10a-hexahydropyrazino-[1,2:a]indoles.

1,2,3,4,10,10a-Hexahydropyrazino[1,2:a]indoles are described in U.S. Pat. No. 3,853,878 and German Offenleg. 21 62 422 and 22 50 493. These compounds have valuable pharmacological properties and can be used as medicaments, particularly for the treatment of hypertension.

Known methods for preparing these substances are unsatisfactory since they require reduction with complex metal hydrides or diborane. Thus, known preparative methods are expensive and dangerous to carry out on an industrial scale. Although these hexahydropyrazinoindoles can be made from the corresponding 2-halomethyindolines, no industrially acceptable method of preparation is known for these intermediates.

SUMMARY OF THE INVENTION

In one aspect this invention relates to novel indoline compounds of Formula I

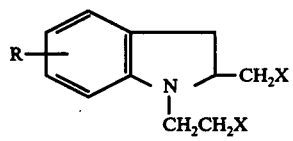

wherein R is H or $CH_3O$ and the X each are Cl or Br or collectively are $N(CH_2C_6H_5)$, and the acid addition salts thereof.

In a preparative aspect, this invention relates to a method of preparing 2-halomethylindolines of the formula

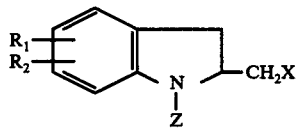

wherein Z is H, saturated or unsaturated or unsaturated alkyl or aryl of up to 20 carbon atoms or saturated or unsaturated alkyl or aryl substituted by halogen, hydroxyl, alkoxy of 1–4 carbon atoms, amino, alkylamino or dialkylamino of up to 4 carbon atoms per alkyl; X is Cl or Br; $R_1$ and $R_2$ independently are H, halogen, alkyl or alkoxy of up to 4 carbon atoms, nitro, amino, alkylamino or dialkylamino of up to 4 carbon atoms per alkyl or $R_1$ and $R_2$ collectively are methylenedioxy, or an acid addition salt thereof, comprising the steps treating a compound of the formula

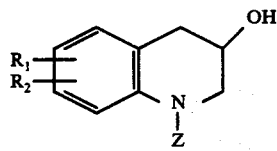

with an inorganic acid halide and converting the resulting acid solution to a free base by reaction with a base or to an acid addition salt by treatment with an acid.

In another preparative aspect, this invention relates to preparing novel indoline compounds of Formula I

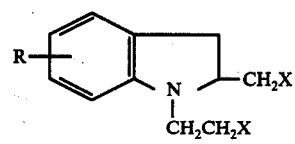

wherein X each are Cl or Br or an acid addition salt thereof and to the further conversion of this product to a 2-benzyl-1,2,3,4,10,10a-hexahydropyrazino [1,2:a]indole by reaction with benzylamine.

DETAILED DESCRIPTION

2-Halomethylindolines, wherein halogen is chlorine or bromine, can be obtained in high yields by treating 3-hydroxy-1,2,3,4,-tetrahydroquinolines with inorganic acid halides:

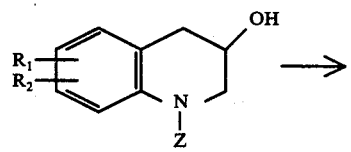

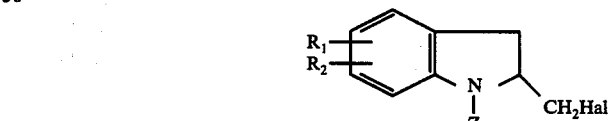

In the preparation of 2-halomethylindolines, wherein halogen is chlorine or bromine, and of acid addition salts thereof, a 3-hydroxy-1,2,3,4-tetrahydroquinoline is treated with an inorganic acid halide and, if appropriate, a resulting acid addition salt is converted by treatment with a base in the free 2-halomethylindoline and, if appropriate, the latter is converted by an acid to an acid addition salt.

The 2-halomethylindolines are formed by ring-contraction to yield hydrochlorides or hydrobromides, from which the free bases can be obtained easily. Z can be hydrogen or, preferably, a hydrocarbon radical, for example, an alkyl or aryl radical of up to 20 carbon atoms, preferably up to 6 carbon atoms. The alkyl can be substituted by halogen including fluorine, chlorine, bromine or iodine; hydroxyl; alkoxy of 1–4 carbon atoms; or amino, alkylamino or dialkylamino of up to 4 carbon atoms per alkyl.

Z can also contain one or more double or triple bonds. It can be a substituted or unsubstituted alkenyl, alkinyl, cycloalkyl, cycloalkenyl or aralkyl group. The starting materials and end products can contain other substituents in the ring system. The benzene ring can be substituted by alkyl or alkoxy groups of up to 4 carbon atoms; fluorine, chlorine, bromine or iodine; nitro; amino, monoalkylamino and/or dialkylamino of up to 4 carbon atoms per alkyl. Preferably, the benzene ring is substituted in the position para- to the nitrogen atom of the heterocycle, that is, the 6-position in the tetrahydroquinolines and the 5-position in the indolines. However, the 8-position in the tetrahydroquinoline derivatives or the 7-position in the indoline derivatives as well as the 4-, 5- and 7-positions in the tetrahydroquinoline derivative and the 3-, 4- and 6-positions in the indoline derivatives can also be substituted.

3-Hydroxy-1,2,3,4-tetrahydroquinolines starting materials can be obtained by known methods from aniline or substituted anilines by reaction with epichlorohydrin or substituted 2-halogenomethylethylene oxides and subsequent cyclization.

References describing the preparation of 3-hydroxy-1,2,3,4-tetrahydroquinolines include German patent no. 619,825 (1934); Journal of Organic Chemistry, 24. 2030 (1959); ibid., 30. 2801 (1965).

Inorganic acid halides which can be used to convert 3-hydroxy-1,2,3,4-tetrahydroquinolines to indoline derivatives include phosphorus oxychloride, phosphorus oxybromide, and halides derived from phosphoric acid, phosphorous acid or sulfurous acid, e.g., phosphorus pentachloride, phosphorus trichloride, phosphorus tribromide, thionyl chloride, and thionyl bromide. Phosphorus oxychloride or oxybromide is preferred.

The reaction can be carried out in an inert solvent. Suitable solvents include hydrocarbons, e.g., benzene, toluene, xylene, petroleum ether or hexane; halogenated hydrocarbons, e.g., methylene chloride, chloroform, carbon tetrachloride, trichloroethylene or 1,2-dichloroethane; and ethers, e.g., diethyl ether, diisopropyl ether, tetrahydrofuran or dioxane. Halogenated hydrocarbon solvents are preferred, particularly chloroform.

The reaction can be done in an excess of the inorganic acid halide. Reaction temperatures are between 0° - 150°. It is sometimes preferable to cool at first, during the exothermic phase of the reaction, and then to heat the mixture to temperatures between about 50° and 100° to complete the reaction. The reaction is preferably carried out using phosphorus oxychloride in chloroform at temperatures between 20° and the boiling point.

As starting materials for the synthesis of hexahydropyrazinoindoles, 1-(2-Y-ethyl)-3-hydroxy-1,2,3,4-tetrahydroquinolines of Formula II

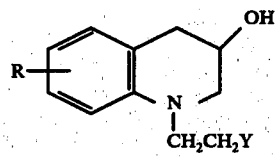

wherein Y is Cl, Br or OH and R is H or CH₃O can be used. The compounds of Formula II can be obtained from N-(2-Y-ethyl)-anilines, such as N-(2-hydroxyethyl)-aniline, and epichlorohydrin.

Treating compounds of Formula II with inorganic acid halides gives the corresponding 1-(2-haloethyl)-2-halomethylindolines. These compounds can be converted by ammonia or primary amines to 1,2,3,4,10,10a-hexahydropyrazino[1,2:a]indoles.

Hexahydropyrazinoindoles unsubstituted at the nitrogen atom in the 2-position, which are particularly important intermediates to the corresponding 2-carboxamidines (see U.S. Pat. No. 3,853,878) are obtained in unsatisfactory yields using ammonia, owing to the side-reactions which occur. They can be prepared preferably by treating the resulting dihalogen compound with benzylamine to give 2-benzyl-1,2,3,4,10,10a-hexahydropyrazino [1,2:a]indole and subjecting the latter to hydrogenolysis, for example, with hydrogen over a palladium catalyst.

The reaction of a dihalo compound of Formula I (X is Cl or Br) with benzylamine can be carried out either in the melt, under pressure, or in an inert solvent or mixture of solvents. Suitable solvents include hydrocarbons, halogenated hydrocarbons and ethers indicated above as well as alcohols, including methanol or ethanol; ethylene glycol mono- and diethers; ketones, e.g., acetone, butanone and diethyl ketone; amides, e.g., dimethylformamide; sulfoxides, such as dimethylsulfoxide, and water. A mixture of acetone and water, particularly in a ratio of 3 : 2, is preferred. Reaction temperatures are between 80° and 150°. The reaction time is about 1-50, preferably 10 to 30 hours.

Acid addition salts of compounds of Formula I include hydrochlorides, hydrobromides, and salts of other strong inorganic or organic acids; for example, sulfates, nitrates, phosphates, methanesulfonates and p-toluenesulfonates. Hydrochlorides and hydrobromides are preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1 a. A solution of 184 ml. of phosphorus oxychloride in 180 ml. of chloroform is added dropwise, with stirring, to a solution of 235 g. of 1-(2-hydroxyethyl)-3-hydroxy-1,2,3,4-tetrahydroquinoline (an oil, hydrobromide, m.p. 167°), obtainable by dropwise addition of 2-anilinoethanol to a solution of epichlorohydrin in isopropanol, boiling for 4 hours, evaporating and heating the residue at 160° for 3 hours in diethylaniline/cyclohexanol, in 355 ml. of chloroform. The mixture is boiled for 2 hours more and cooled. Excess phosphorus oxychloride is decomposed by adding 600 ml. of water dropwise. The phases are separated and the aqueous phase is extracted several times with chloroform, washed with water until neutral and evaporated to give 1-(2-chloroethyl)-2-chloromethylindoline hydrochloride, an oil, which is converted directly to the free base, b.p. 132°-135°/0.05 mm.

b. 200 ml. of water and 0.5 g. of potassium iodide are added to a solution of 130 g. of 1-(2-chloroethyl)-2-chloromethylindoline hydrochloride in 300 ml. of acetone. To this are added 240 g. of benzylamine and the mixture is boiled for 16 hour and evaporated. The residue is dissolved in 15% hydrochloric acid and the solution is washed with toluene and extracted several times with chloroform. The combined chloroform phases are washed with water, then with 20% sodium hydroxide solution and again with water and are evaporated. The resulting oily 2-benzyl 1,2,3,4,10,10a-hexahydropyrazino[1,2:a]indole is dissolved in methanol. Passing in gaseous hydrogen bromide gives the hydrobromide, m.p. 231°.

EXAMPLE 2

Following the procedure of Example 1, 1-(2-hydroxyethyl)-3-hydroxy-5-methoxy-1,2,3,4-tetrahydroquinoline, obtainable from 2-p-methoxyanilinoethanol and epichlorohydrin, and phosphorus oxychloride gives 1-(2-chloroethyl)-2-chloromethyl-5-methoxyindoline. The latter reacts with benzylamine to give 2-benzyl-8- methoxy-1,2,3,4,10,10a-hexahydropyrazino[1,2:a]indole.

EXAMPLE 3

1-(2-Hydroxyethyl)-3-hydroxy-1,2,3,4-tetrahydroquinoline is reacted according to Example 1a, with an equivalent quantity of phosphorus oxybromide in chloroform to produce 1-(2-bromoethyl)-2-bromomethylindoline hydrobromide, an oil. This crude oil is reacted, following Example 1b, with benzylamine to give 2-benzyl-1,2,3,4,10,10a-hexahydropyrazino[1,2:a]-indole. Hydrobromide, m.p. 231°.

EXAMPLE 4

The following are obtained, following Example 1a, from 1-methyl-, 1-ethyl-, 1-n-butyl-, 1-n-hexyl-, 1-allyl-, 1-phenyl-, 1-benzyl-, 1-(2-chloroethyl)-, 1-(3-chloropropyl)-, 1-(2-methoxyethyl)-, 1-(2-aminoethyl)- and 1-(2-dimethylaminoethyl)-3-hydroxy-1,2,3,4-tetrahydroquinoline, respectively, and phosphorus oxychloride:

1-methyl-2-chloromethylindoline, b.p. 95°–100°/0.2 mm;
1-ethyl-2-chloromethylindoline, b.p. 110°/0.1 mm;
1-n-butyl-2-chloromethylindoline;
1-n-hexyl-2-chloromethylindoline;
1-n-allyl-2-chloromethylindoline;
1-phenyl-2-chloromethylindoline;
1-benzyl-2-chloromethylindoline;
1-(2-chloroethyl)-2-chloromethylindoline;
1-(3-chloropropyl)-2-chloromethylindoline;
1-(2-methoxyethyl)-2-chloromethylindoline;
1-(2-aminoethyl)-2-chloromethylindoline, and
1-(2-dimethylaminoethyl)-2-chloromethylindoline.

EXAMPLE 5

The following are obtained, following Example 1a, from 1-(2-hydroxyethyl-3-hydroxy-4-methyl-, -5-methyl-, -6-methyl-, -7-methyl-, -8-methyl-, -6-ethyl-, -5-methoxy-, -7-methoxy-, -8-methoxy-, -6-ethoxy-, -6-fluoro-, -6-chloro-, -6-bromo-, -6-iodo-, -6-trifluoromethyl-, -6-nitro-, -6-amino-, -6-methylamino-, -6-dimethylamino-, -6,7-dimethoxy- or -6,7-methylenedioxy-1,2,3,4-tetrahydroquinoline, respectively, and phosphorus oxychloride:

1-(2-chloroethyl)-2-chloromethyl-3-methylindoline;
1-(2-chloroethyl)-2-chloromethyl-4-methylindoline;
1-(2-chloroethyl)-2-chloromethyl-5-methylindoline, b.p. 155°/0.01 mm;
1-(2-chloroethyl)-2-chloromethyl-6-methylindoline;
1-(2-chloroethyl)-2-chloromethyl-7-methylindoline;
1-(2-chloroethyl)-2-chloromethyl-5-ethylindoline;
1-(2-chloroethyl)-2-chloromethyl-4-methoxyindoline;
1-(2-chloroethyl)-2-chloromethyl-6-methoxyindoline;
1-(2-chloroethyl)-2-chloromethyl-7-methoxyindoline;
1-(2-chloroethyl)-2-chloromethyl-5-ethoxyindoline;
1-(2-chloroethyl)-2-chloromethyl-5-fluoroindoline;
1-(2-chloroethyl)-2-chloromethyl-5-chloroindoline;
1-(2-chloroethyl)-2-chloromethyl-5-bromoindoline;
1-(2-chloroethyl)-2-chloromethyl-5-iodoindoline;
1-(2-chloroethyl)-2-chloromethyl-5-trifluoromethylindoline;
1-(2-chloroethyl)-2-chloromethyl-5-nitroindoline;
1-(2-chloroethyl)-2-chloromethyl-5-aminoindoline;
1-(2-chloroethyl)-2-chloromethyl-5-methylaminoindoline;
1-(2-chloroethyl)-2-chloromethyl-5-dimethylaminoindoline;
1-(2-chloroethyl)-2-chloromethyl-5,6-dimethoxyindoline, and
1-(2-chloroethyl)-2-chloromethyl-5,6-methylenedioxyindoline.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

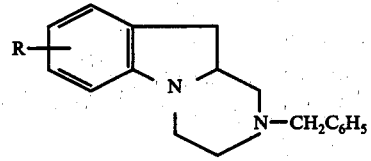

wherein R is H or CH₃O, or an acid addition salt thereof.

2. 2-Benzyl-1,2,3,4,10,10a-hexahydropyrazino [1,2:a]-indole, a compound of claim 1.

3. 2-Benzyl-1,2,3,4,10,10a-hexahydropyrazino [1,2:a]-indole hydrobromide, a compound of claim 1.

4. A compound of claim 1 wherein R is CH₃O.

5. 2-Benzyl-8-methoxy-1,2,3,4,10,10a-hexahydropyrazino[1,2:a]-indole, a compound of claim 1.